United States Patent
Bagwell et al.

[11] Patent Number: 5,301,662
[45] Date of Patent: Apr. 12, 1994

[54] NEBULIZER WITH HIGH OXYGEN CONTENT AND HIGH TOTAL FLOW RATE

[75] Inventors: James T. Bagwell, Anaheim; Blair E. Howe, Rancho Santa Margarita, both of Calif.

[73] Assignee: Cimco, Inc., Costa Mesa, Calif.

[21] Appl. No.: 765,133

[22] Filed: Sep. 25, 1991

[51] Int. Cl.⁵ .............................................. A61M 11/00
[52] U.S. Cl. ........................... 128/200.14; 128/200.18; 128/200.21; 128/205.11
[58] Field of Search ....................... 128/200.14, 200.16, 128/200.18, 203.25, 203.26, 203.27, 205.11, 200.21; 261/DIG. 65

[56] References Cited

U.S. PATENT DOCUMENTS

| | | | |
|---|---|---|---|
| 3,353,536 | 11/1967 | Bird et al. | 128/194 |
| 3,527,411 | 9/1970 | Colgan | 239/338 |
| 3,744,771 | 7/1973 | Deaton | 261/78 |
| 3,836,079 | 9/1974 | Huston | 261/DIG. 65 |
| 3,857,909 | 12/1974 | Huggins | 261/DIG. 65 |
| 3,874,379 | 4/1975 | Enfield et al. | 128/194 |
| 3,901,443 | 8/1975 | Mitsui et al. | 261/DIG. 65 |
| 4,007,238 | 2/1977 | Glenn | 261/78 |
| 4,101,611 | 7/1978 | Williams | 261/142 |
| 4,116,387 | 9/1978 | Kremer, Jr. et al. | 239/338 |
| 4,195,044 | 3/1980 | Miller | 128/203.26 |
| 4,267,974 | 5/1981 | Kienholz et al. | 128/200.21 |
| 4,299,355 | 11/1981 | Häkkinen | 239/338 |
| 4,427,004 | 1/1984 | Miller | 128/203.25 |
| 4,595,002 | 6/1986 | Michaels et al. | 261/DIG. 65 |
| 4,612,926 | 9/1986 | Boiarski et al. | 128/200.21 |
| 4,629,590 | 12/1986 | Bagwell | 128/200.21 |
| 4,767,576 | 8/1988 | Bagwell | 128/200.18 |
| 4,819,625 | 4/1989 | Howe | 128/200.18 |
| 4,911,157 | 3/1990 | Miller | 128/203.25 |
| 5,040,532 | 8/1991 | Alfery | 128/205.11 |
| 5,063,921 | 11/1991 | Howe | 128/203.26 |

*Primary Examiner*—Edgar S. Burr
*Assistant Examiner*—Aaron J. Lewis
*Attorney, Agent, or Firm*—Poms, Smith, Lande & Rose

[57] ABSTRACT

An air entrainment nebulizer obtains a high oxygen content with an optimum total flow rate by employing an oxygen jet large enough to flow about 40 liters a minute of pressurized oxygen and an air entrainment opening of a very small total size. The air entrainment opening is a configured for very fine incremental adjustment adjacent the minimal opening or nearly closed position so as to readily control oxygen content of the discharged moisturized mixture without excessively increasing total flow rate. The air entrainment aperture is divided several parallel mutually staggered elongated slots, each having a width sufficiently small to block projection of water droplets from the mixing chamber. The combination of a high flow rate oxygen jet and a small size air entrainment aperture provides a discharge outlet having oxygen percentages in the range of about 60% to nearly 100% while maintaining a total output flow rate in the order of about 40 to about 70 liters per minute.

11 Claims, 3 Drawing Sheets

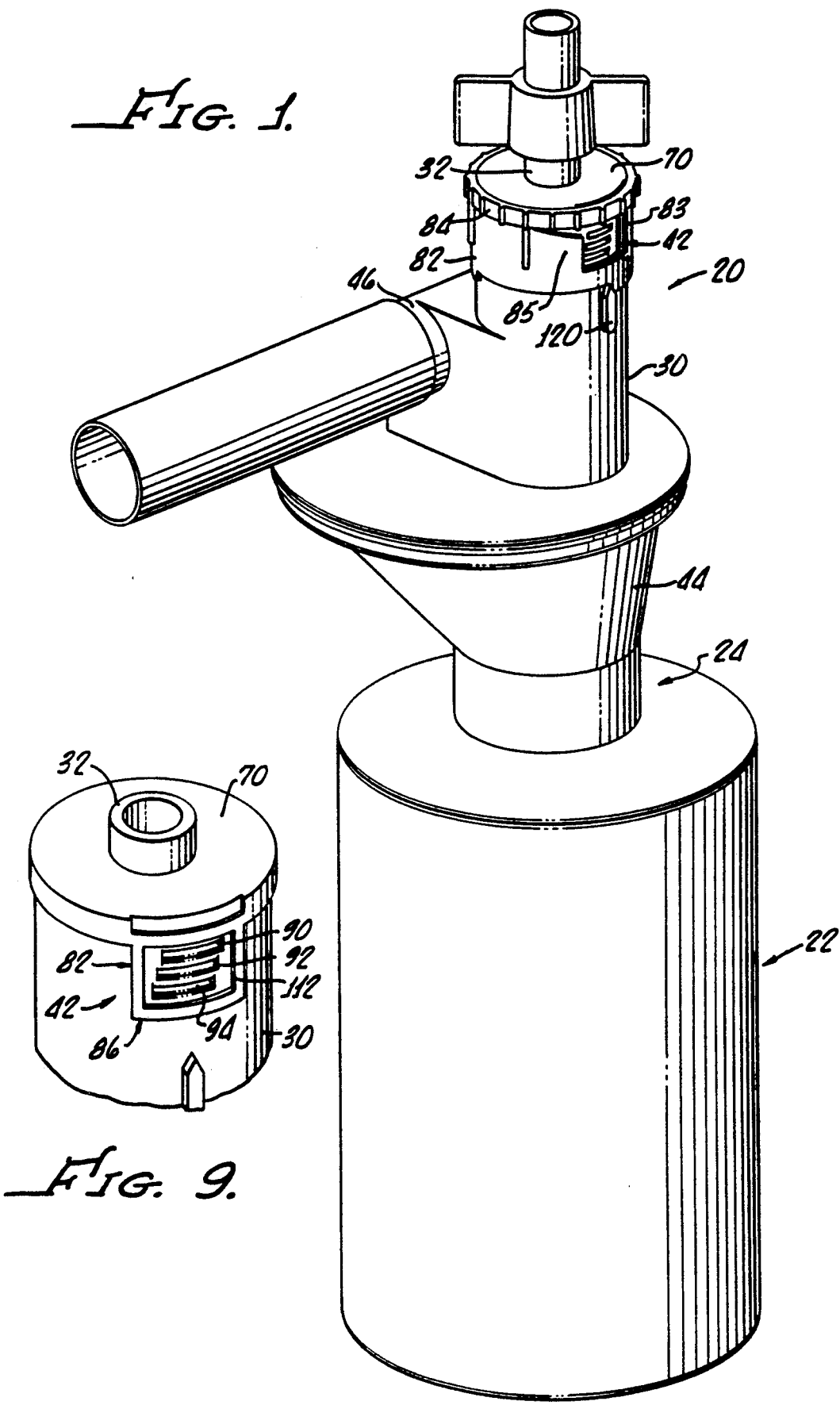

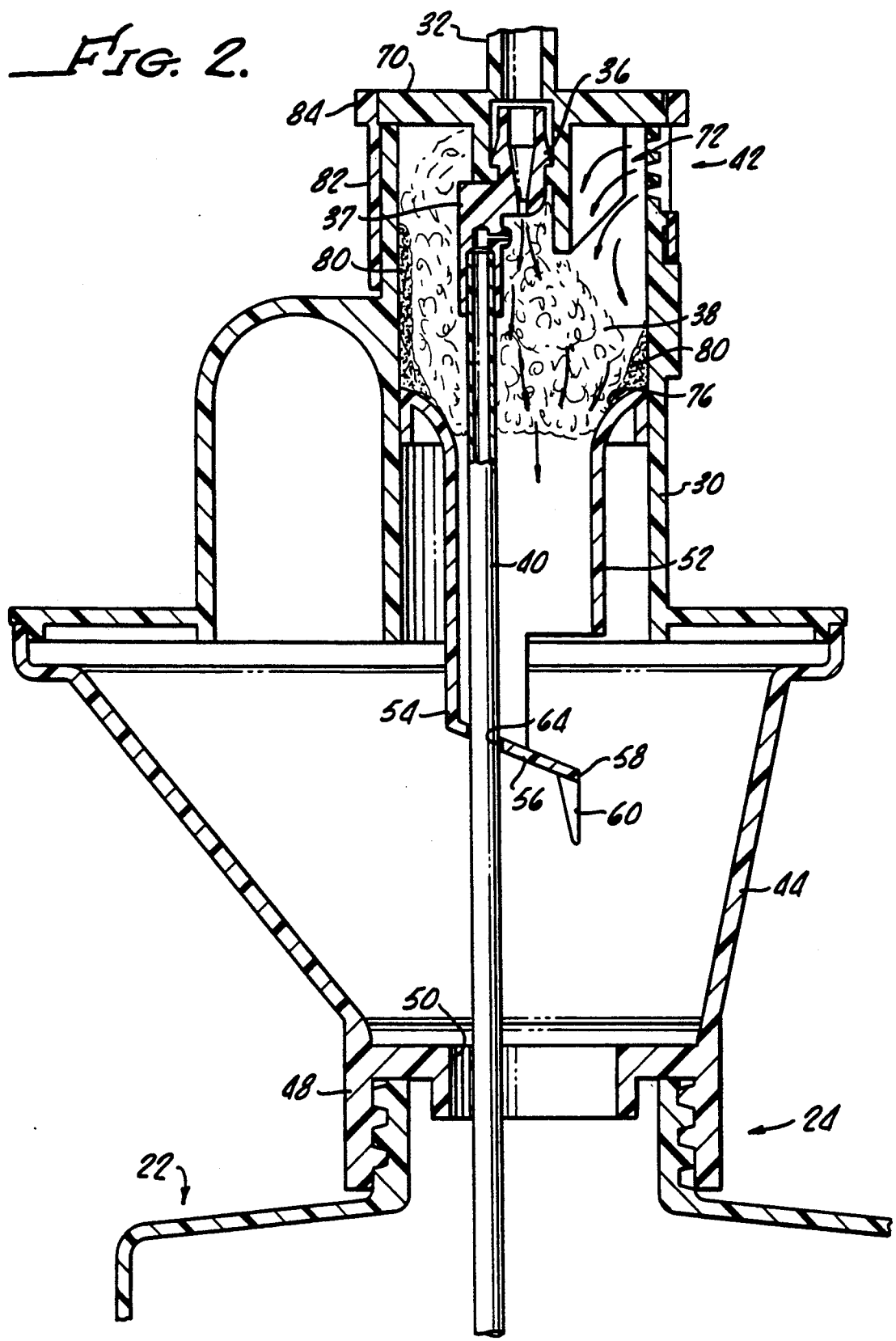

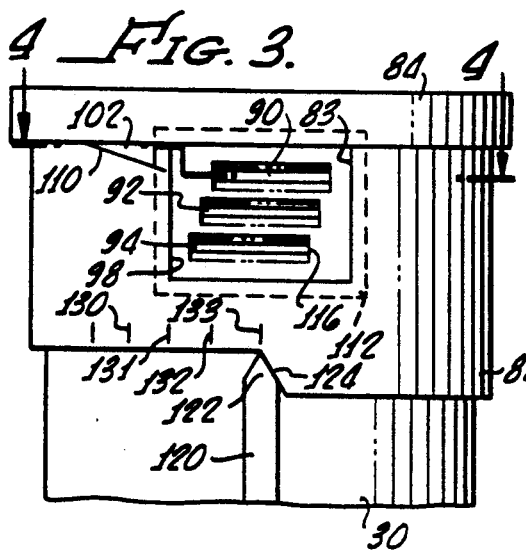
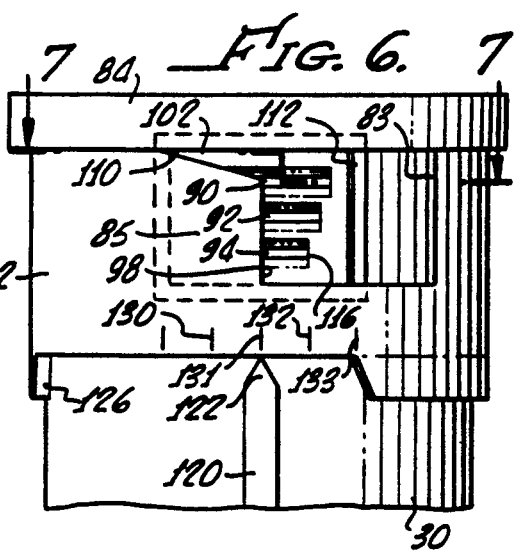
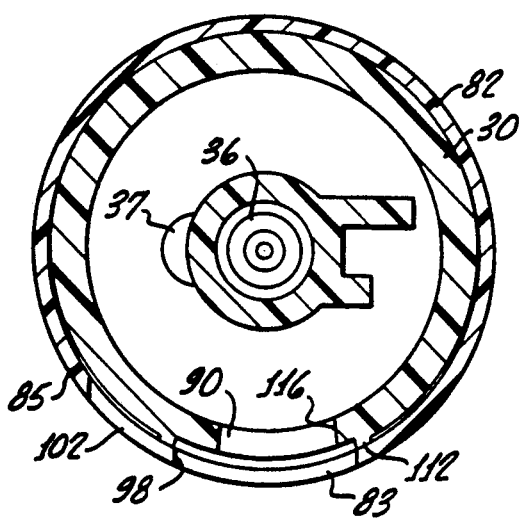
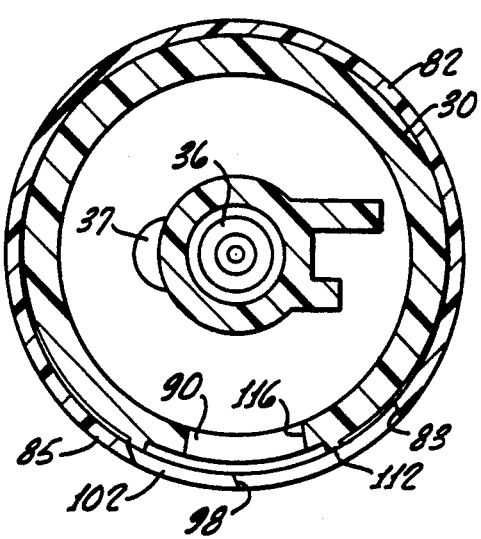
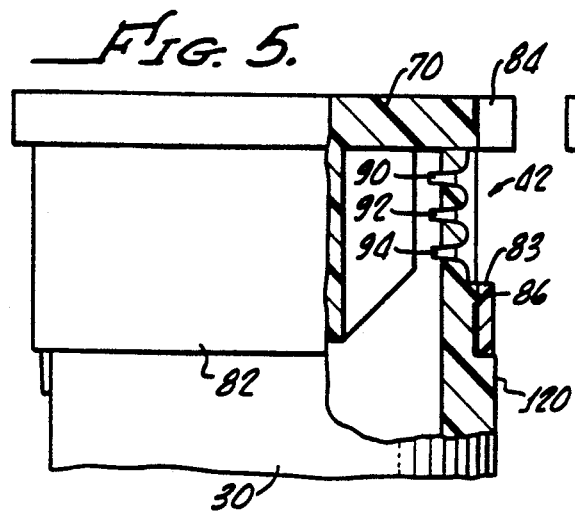
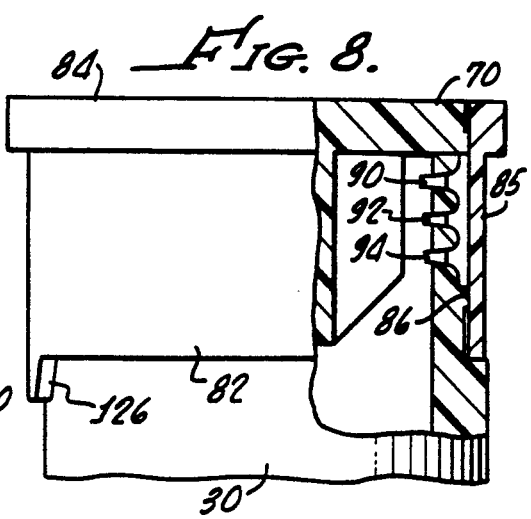

NEBULIZER WITH HIGH OXYGEN CONTENT AND HIGH TOTAL FLOW RATE

BACKGROUND OF THE INVENTION

1. Field of the Invention

The present invention relates to air entrainment nebulizers and more particularly concerns a nebulizer that provides a range of high oxygen content with optimum total output flow rate.

2. Description of Related Art

In common forms of inhalation therapy, an oxygen enriched air mixture is provided for introduction into a patient's lungs by means of suitable breathing apparatus. The gas mixture is preferably moisturized and transmitted to the patient through a flexible tube which may be several feet or more in length. The nebulizer provides a gas stream that entrains water particles rather than water vapor (as in a humidifier). Minimum water particle size is required to ensure that water will reach deeper portions of the respiratory tract. A nebulizer is used to provide a gas mixture that may be selectively varied from a high oxygen content, nearly 100% in some cases, to as little as 28%. A nebulizer with a wide range of oxygen percentages is described in U.S. Pat. No. 4,767,576 entitled "Nebulizer With Auxiliary Gas Input". In the arrangement of this nebulizer, pressurized oxygen is fed to a mixing chamber through a first nozzle and pressurized air is fed to the mixing chamber from a second nozzle so that the total flow rate, e.g. the flow rate of oxygen and the flow rate of air, can be readily controlled. Therefore, by controlling flow rate of both pressurized gaseous inputs to the mixing chamber, the total flow rate that is discharged from the nebulizer can be readily controlled. Flow rates of the oxygen and pressurized gas are controlled by metering valves on the input tubing, as is well known. The nebulizer with the auxiliary gas input, although effective for its purpose, is not useful where a pressurized auxiliary air source is not available. In some hospitals and similar facilities, only pressurized oxygen outputs are provided so that a nebulizer with the auxiliary gas input as described in U.S. Pat. No. 4,767,576 cannot be employed.

A nebulizer that uses solely a pressurized oxygen input depends upon air entrainment for auxiliary gas or air input as is described, for example, in U.S. Pat. No. 4,629,590 for "Nebulizer." In the nebulizer of U.S. Pat. No. 4,629,590, pressurized oxygen is fed through a jet that produces a lowered pressure for entrainment of water from a container which is thus drawn into a mixing chamber having a pair of apertures that are adjusted by a rotating sleeve. The nebulizer of U.S. Pat. No. 4,629,590 employs an oxygen jet capable of flowing up to about 15 liters per minute of oxygen and achieves adjustment of oxygen content of the discharged mixture by varying the air entrainment apertures in the mixer body. However, oxygen content above about 60% of the output mixture cannot be obtained with the air entrainment nebulizer of U.S. Pat. No. 4,629,590 without providing an unacceptably low total output flow rate. This nebulizer is provided with a limited oxygen flow rate jet and thus is not capable of producing high flow rates of oxygen. However, even if it should be used with an oxygen jet capable of higher oxygen flow rates, much greater quantities of air are pulled into the mixing chamber through the air entrainment ports and thus total output flow rates well over 100 liters per minute or sometimes as high as 140 or 150 liters per minute would be provided if a larger oxygen jet were used to flow 30 or 40 liters per minute of oxygen to the mixing chamber. Also, though the nebulizer with the auxiliary gas input can provide high oxygen percentages at optimum flow rate, this instrument can be used only where there is a source of auxiliary gas input. The nebulizer of U.S. Pat. No. 4,629,590, on the other hand, can be used wherever there is solely a source of pressurized oxygen and is not dependent upon the availability of pressurized auxiliary gas. However, this nebulizer can provide output mixtures having only limited (not more than about 60%) percentages of oxygen with useful total flow rates.

In fact, where an air entrainment nebulizer of the type shown in U.S. Pat. No. 4,629,590 is employed, high oxygen content (above about 60%) at useful flow rates (e.g. between about 40 to 70 liters per minute) can be achieved only by employing two similar nebulizers of this type and combining their outputs by a tubing "Y" connection. This is so because when such an air entrainment nebulizer is adjusted for an oxygen percentage above 60%, its air intake is so restricted that its total output flow rate is too small to be useful without being combined with output of a second similarly adjusted air entrainment nebulizer. With the air entrainment nebulizer of U.S. Pat. No. 4,629,590, even with limited total output flow rates, the instrument may be subject to back pressure in the order of 3 to 5 cm of water when the patient either is exhaling or is between breaths. Such back pressures tend to cause the water droplets that are swirling around the mixing chamber to be projected outwardly through the air entrainment openings, thereby causing an undesirable "spitting" which degrades operation of the nebulizer.

Accordingly, it is an object of the present invention to provide an air entrainment nebulizer that avoids or minimizes above-mentioned problems.

SUMMARY OF THE INVENTION

In carrying out principles of the present invention in accordance with a preferred embodiment, an air entrainment nebulizer includes a mixing body having a mixing chamber and a pressurized gas input fitting. A gas jet is connected to the fitting for projecting a high velocity stream of gas into the chamber and has a orifice sufficient to flow pressurized gas at a rate of well over 15 liters per minute. An air entrainment opening or port in the body is made with a maximum open area sufficiently small to flow air into the chamber at a maximum rate not greater than about 40 liters per minute when pressurized gas flows through the jet orifice at about a rate of 40 liters per minute. According to a feature of the invention, the air entrainment opening is formed of a plurality of apertures, each of which has an area small enough to block projection of water droplets through the opening. In accordance with another feature of the invention, an adjustment is provided for the size of the air opening having a fine adjustment portion adjacent its closed position. An adjustable closure is provided for the opening that progressively blocks and unblocks the opening to decrease the open area of the air opening in a non-linear arrangement so as to effect a rate of change of the open area that decreases as the closure moves toward its closed position. This controls the rate of air flow into the entrainment opening so as to allow for precision adjustment in very small amounts as the closure approaches the closed position.

BRIEF DESCRIPTION OF THE DRAWING

FIG. 1 is a pictorial illustration of a nebulizer assembly incorporating principles of the present invention;

FIG. 2 is a vertical sectional view of the nebulizer of FIG. 1;

FIG. 3 is a side elevational view of the air entrainment opening with its closure sleeve in fully opened position;

FIG. 4 is a section taken on lines 4—4 of FIG. 3;

FIG. 5 is a vertical section with parts broken away showing the air entrainment opening and closure sleeve in the position of FIGS. 3 and 4;

FIGS. 6, 7 and 8 respectively correspond to the side elevation view, horizontal section and vertical view with parts broken away, of FIGS. 3, 4 and 5, but showing the closure sleeve and closure member in partly closed position; and FIG. 9 is a pictorial illustration of the upper portion of the mixer body with the closure sleeve removed.

DESCRIPTION OF THE PREFERRED EMBODIMENT

The nebulizer to be disclosed herein is similar to that illustrated in FIGS. 5 through 10 of a co-pending application Ser. No. 422,310 entitled "Nebulizer Heater" invented by Blair E. Howe and assigned to the assignee of the present application. The disclosure of this application is incorporated by this reference as though fully set forth herein. The nebulizer described herein includes a separate nebulizer mixing head and a separate sterile water container, with the nebulizer head being readily adapted for connection to many different types of water containers. Alternatively, the nebulizer head may be made as a unit having its own non-separate sterile water container. As shown in FIGS. 1 and 2, a separate nebulizer head and mixing means is identified generally by numeral 20 and is combined with a separate and independent sterile water container 22 to which it may be detachably secured by a threaded fitting generally indicated by a fitting that is connected to a neck 24 of the mixing head. The nebulizer mixer head comprises a mixer body or housing 30 having an input fitting 32 to which may be connected a hose (not shown, and which itself is connected with a source of pressurized oxygen, not shown). Mixer body 30 includes an internal nozzle fitting 36 having a high velocity jet orifice introducing a high velocity stream of pressurized oxygen from fitting 32 to the interior 38 of the mixer body. Interior 38 forms a mixing chamber in which air, oxygen and water are mixed. A suction tube 40 extends downwardly through all the components, downwardly through the mixing head and into the container 22. The lower end of the suction tube is submerged in a body of liquid (generally sterile water) confined in container 22. A novel air entrainment opening or port 42, to be described in detail below, is formed in mixer body 30 for introducing ambient air into the interior of the mixer body to be mixed with oxygen and water.

Mixer body 30 includes a downwardly tapered aerosol mixing chamber housing section 44 (FIG. 2) in communication with the interior 38 of body 30, and an output fitting 46 (FIG. 1) for discharging mixed aerosol from the aerosol mixing chamber section 44. The lower end of chamber 44 is formed with an internally threaded connecting nipple 48 and at its lower end, has a relatively large diameter passage 50 allowing water droplets precipitated from aerosol within the mixing chamber 44 to flow or fall downwardly from the chamber. A venturi tube 52 is mounted to the interior of body 30 to increase flow velocity of aerosol into the mixing chamber 44. The venturi tube also provides improved precipitation droplet collection. The venturi tube is fixedly positioned within the mixer body below the jet orifice of nozzle fitting 36 and has a lowermost portion 54 of its shank cut-away to form a large lateral opening. One side of the venturi tube shank fixedly supports an inclined bottom plate 56, inclining downwardly toward one of the walls (toward the right as viewed in FIG. 2) of mixing chamber 44. The lowermost free edge 58 of plate 56 has a downwardly projecting wedge shaped and pointed drip member 60 fixed thereto. The plate also has an aperture 64 that snugly receives suction tube 40.

The venturi tube 52 acts to increase velocity of the gas jet projected from nozzle fitting 36 and also, by means of its bottom plate 56, collects falling water droplets. These collected droplets move to the free edge of the plate and then along the drip wedge 60. Droplets fall from the point at the lower end of drip wedge 60.

Droplets in the aerosol tend to collect on various surfaces including surfaces of the suction tube above the bottom plate 56. The snug fit of the bottom plate hole around the exterior of the suction tube blocks further downward flow of collected droplets on the exterior of the suction tube and diverts these droplets along the bottom plate to the drip wedge and then back into the container.

Fixed to and depending from the interior surface of upper end 70 of the mixer body is a channel shaped baffle or air deflector 72, substantially similar to that described in U.S. Pat. No. 4,767,576. The deflector receives and redirects incoming air that is pulled into the jet mixing chamber 38 through the air entrainment opening port 42. The arrangement provides a greatly increased turbulence of swirling air, oxygen and water within the chamber 38 which is increased at least in part by impingement of the downwardly projected oxygen jet upon the venturi tube entrance surface 76. The arrangement provides a buildup around the interior tubular wall of mixer body 30 of a wall of turbulent "standing" water, generally indicated at 80, which completely fills the mixing chamber above the upper end of the venturi tube 52. The arrangement thus can collect and hold larger water droplets within the turbulent mixture.

A circular sleeve 82, having a serrated upper circumferential edge 84 to facilitate manual rotation, is mounted for circumferential sliding rotation on the upper end of mixer body 30 and includes a closure port 83. A closure shield portion 85 is provided adjacent closure port 83 to adjustably overlie the opening 42 in the mixer body. Opening 42, as can be best seen in FIGS. 3, 5, 6, 8 and 9, is framed by a rectangular perimetral ridge 86 that projects outwardly of the outer surface of the mixer body by a very small distance of about 0.015 inches. The ridge helps to hold the closure sleeve and its closure shield 82 spaced slightly away from the outer surface of the mixer body.

The air entrainment opening 42 in the mixer body is formed of a group of three mutually parallel but mutually longitudinally staggered narrow slots 90, 92, and 94 (FIGS. 3, 5, 6, 8 and 9) that extend circumferentially around the body of the mixer within the area framed by ridge 86. Each slot in the presently preferred embodiment has a length of about 0.33 inches and has a width at its radially inner end of about 0.025 inches whereby the open area of each slot is 0.00925 square inches to provide a total open area for all three slots of about 0.025 square inches.

In operation of the described nebulizer, the rotatable sleeve or dial 82 is adjusted until the desired percentage of oxygen in the output mixer is indicated by the point of an indicator bar 120 fixed on housing 30. A flow rate of oxygen to input fitting 32 is then selected by adjustment of a metering valve (not shown) to cause a flow of oxygen into the jet fitting 36 at a rate of about 30 to 40 liters per minute. The jet stream of oxygen projected from the nozzle produces a decreased pressure adjacent a water aspirating fitting 37 connected to the upper end of aspirating tube 40 so that the decreased pressure at the nozzle output orifice sucks water from container 22 up into the chamber 38. Concomitantly, the lowered pressure within the chamber 38 sucks air in through the air entrainment opening 42. Incoming air flows into and against deflector 72 to be directed downwardly toward entrance surface 76 of the venturi tube 52. The venturi tube directs the mixture of air, water and oxygen downwardly through its throat to the mixing chamber 44 to impinge upon plate 56 and to be redirected in a swirling motion around the chamber 44. This operation is essentially the same as that described in the patents and patent application identified above, except for the fact that (a) the flow rate of input oxygen is much greater, and (b) the flow rate of input air through the uniquely configured and restricted opening 42 is much smaller and more precisely adjustable. After selecting a given flow rate of oxygen, a desired percentage of oxygen in the output mixture from output fitting 46 is obtained by rotating adjustment of the closure sleeve 82. This adjustment changes the size of the total open area of the opening 42 to change the percentage of oxygen in the output mixture. Even though a very high oxygen percentage may be obtained, the total flow rate of the output mixture remains at an optimum value, as will be more particularly explained in connection with Table I below.

The several slots 90, 92, 94 are staggered by a very small amount, which may be in the order of about 0.030 inches, for example, so that each slot is offset longitudinally of an adjacent slot by this amount. The mixer body is preferably formed by standard injection molding techniques and therefore the several slots are tapered from outside to inside, as viewed in the cross sections of FIGS. 5 and 8. The tapered slots have slightly larger outer dimensions and portions between the slots are rounded for ease of molding operation.

A closure shield 85 of the slidable sleeve 83 has a free edge 98 that forms one side of a primary opening 83 in the sleeve. This opening 83 is nearly co-extensive with, but is slightly smaller than the area circumscribed by the ridge 86. Opening 83 of the sleeve is formed with a tapered triangular fine adjustment portion 102 that extends circumferentially from the edge 98 to a point 110 so that the described opening of the slidable shield has a wedge shaped extended portion that tapers to a smaller area as it is further away from the major portion of the opening. The arrangement of the staggered slots and tapered extension of the closure member opening collectively provide for a fine adjustment of the size of the air opening as the closure member approaches a closed position. FIG. 3 shows the closure member in full open position (where the closure member contacts a minimum portion of ridge 86), whereas FIG. 6 shows the closure member in an intermediate position. The slidably rotatable closure shield can move from the fully open position illustrated in FIG. 3 to a fully closed position (not shown) in which the small end 110 of the wedge shaped open area 102 is positioned at or beyond (to the right as viewed in FIG. 6) of the ridge element 112. In the intermediate position that is shown in FIG. 6, the closure shield 84 has nearly fully closed the lowermost slot 94 as the closure member moves toward the right as viewed in FIG. 6. Further motion of the closure sleeve to the right from the position in FIG. 6 will decrease the open area of only the upper 2 slots, namely slots 90 and 92 after slot 94 has been completely closed. So too, in a similar manner, when the edge 98 of the closure shield 84 reaches the right hand end of slot 92, both of the lower slots 92 and 94 have been completely closed so that further motion toward fully closed position will further close only portions of the single slot 90. Still further, after the leading edge 98 of the closure member has reached the end of the uppermost slot 90 all or substantially all of all three slots are closed but a small area of uppermost slot 90 is still in registry with a portion of the wedge tapered opening 102 of the sleeve opening so that a very small amount of slot 90 is still open. In this position the closure member contacts all or a major portion of ridge 86 and contacts ridge element 112.

Thus, it can be seen that when the closure sleeve is moving from left to right as viewed in FIGS. 3 and 6 toward the closed position, it will initially close a small portion of the lowermost slot 94 or the motion will cause the closure member to block portions of the lower two slots and still further, portions of the lower three slots. However, the fine adjustment of this substantially fully opened position is not of great significance. When the closure member is blocking only portions of all three slots, the rate of decrease of the total open area is substantially linear and is substantially proportional to the distance that the closure member has moved toward the closed position. However, when the closure member has its leading edge 98 substantially adjacent to or at the far end 116 of lowermost slot 94, the closure has reached a fine adjustment position in which the decrease of the open area becomes nonlinear so that the rate of decrease of the open area with respect to the rate of motion of the sliding sleeve is less than it is at other (more open) positions of the closure member. The nonlinearity of the rate of decrease of open area is due in part to the fact that only two of the three slots are open and, further, to the decreasing open area of the wedge shaped section 102.

Indicator bar 120 is formed in and projects slightly outwardly from the surface of mixer body 38 and has a pointed end 122 that cooperates with a cut-away portion 124 on one side of the sleeve to limit the sleeve to its fully open position and which cooperates with a second cut-away portion 126 to limit rotation of the sleeve to its maximum or fully closed position. A suitable scale with numbers (not shown) is formed or printed on the exterior surface of the slidable sleeve and includes indicating lines 130, 131, 132 and 133 which cooperate with the point of marking bar 120 to represent positions in which the oxygen content of the output mixer is respectively 85%, 75%, 65% and 60% in a particular embodiment of the invention that has been constructed and tested.

The size and configuration of the air entrainment opening and its closure arrangement as illustrated and disclosed herein enable the use of a high flow rate of input pressurized oxygen with the precise control of input flow rate of entrained air so as to enable the instrument to provide an output flow mixture of very high oxygen content at a reasonable total output flow rate. Despite the total overall very small size of the air entrainment opening 42 (its maximum open area), the latter is subdivided into several openings, each of a dimension small enough to prevent "spitting" or the projection of water droplets from the mixing chamber outwardly through the opening when the instrument experiences back pressure in its discharge hose of as much as 4 or 5 cm of water.

An embodiment of the overall system has been tested at various flow rates with results that are indicated in Table 1 for an instrument having the configuration disclosed herein.

TABLE 1

| 1<br>Dial $O_2$ % | 2<br>Actual $O_2$ % | 3<br>$O_2$ Flow | 4<br>Entrained Airflow | 5<br>Total Output Flow |
|---|---|---|---|---|
| 60 | 64.2 | 40 | 33.07 | 73.07 |
| 60 | 62.3 | 30 | 27.32 | 57.32 |
| 60 | 60.4 | 25 | 25.06 | 50.06 |
| 60 | 59.3 | 20 | 21.20 | 41.20 |
| 65 | 63.7 | 30 | 25.44 | 55.44 |
| 65 | 66 | 40 | 30.16 | 70.16 |
| 75 | 73.4 | 30 | 15.2 | 45.2 |
| 75 | 75.3 | 40 | 18.16 | 58.16 |
| 85 | 84.3 | 30 | 7.43 | 37.43 |
| 85 | 83.2 | 40 | 10.79 | 50.79 |
| 98 | 97.5 | 40 | 1.31 | 41.31 |

In Table 1, the first column, Dial $O_2$%, represents the percentage of oxygen that is set by the dial, that is, by rotation of the sleeve 82 to cause the point of the indicator bar 120 to align with an appropriate number (oxygen percentage) printed on the sleeve as represented by indicia 130 through 133. The second column of the table, Actual $O_2$%, indicates the actual percentage of oxygen measured in the output discharge mixture. The third column, $O_2$ Flow, represents the flow rate in liters per minute of oxygen fed to the jet fitting 36 via an input metering valve (not shown). The fourth column, Entrained Airflow, represents the total amount of air (measured) that is pulled into the mixing chamber 38 through the controlled air entrainment opening, in liters per minute. The fifth column, Total Output Flow, represents the total flow rate in liters per minute of the mixture discharged from the instrument.

The desired goal of an instrument of this type is to provide a total output flow in the order of about 40 to 50 liters per minute at a relatively high (60% and above) oxygen percentage. No prior instrument has been able to achieve such a goal without a controlled pressurized air injection combined with controlled oxygen injection. It can be seen from Table 1, for example, that with an oxygen flow rate (column 3) of 30 liters per minute and a dial position (column 1) of 60%, actual oxygen percentage is 62.3% (column 2) with entrained air flow of 27.32 liters per minute (column 4) to provide a total output flow of 57.32 liters per minute (column 5) (which is the sum of the total oxygen flow rate and the total entrained air flow rate. The 60% $O_2$ dial position is the full open position shown in FIG. 4. For a dial position of 65%, and actual oxygen at 30 liters per minute, actual oxygen percent was measured at 63.7% to provide a total output flow rate of 55.44 liters per minute with 25.44 liters per minute of entrained air flow. For a dial position of 75% oxygen, total output flow rate is 45.2 liters per minute with an oxygen flow rate of 30 liters per minute to provide an oxygen content of 73.4% in the output while the system pulled in air at a rate of only 15.2 liters per minute. At higher dial positions, such as an 85% $O_2$ dial position, actual oxygen content is 84.3% with a 30 liter per minute flow rate and only a very small amount of air, 7.43 liters per minute is pulled in through the now almost completely closed opening to provide a total flow rate of 37.43 liters per minute. At a dial position of maximum or nearly maximum oxygen content, the actual or measured oxygen percentage is 97.5% with an oxygen flow rate of 40 liters per minute. In this dial position, the air entrainment opening is closed down so much that only 1.31 liters per minute of air is pulled in to provide a total output flow rate of 41.31 liters per minute.

These high oxygen percentages are available in the described nebulizer with optimum total output flow rates of around 40 to 50 liters per minute. This operation is made possible by use of the larger oxygen jet (which permits 30 to 40 liters per minute of oxygen to be flowed into the mixing chamber), together with a very much smaller air entrainment opening and its fine precision adjustment at or near the fully closed position. It may be noted from Table 1 that the total area of the air adjustment opening is small enough so that even at 60% oxygen percentage dial position (fully open position of the closure sleeve) and at 40 liters per minute of oxygen input, the total output flow is still only about 73 liters per minute or with a dial position of 60% and an oxygen flow of 30 liters per minute. The total output flow rate can be dropped to 50.06 liters per minute, which is close to a desirable range, by decreasing the oxygen flow rate in this 60% dial position to 25 liters per minute. Further, by moving the dial from 85% $O_2$ to 98% $O_2$, the air input is changed by only a very small amount, from 10.79 liters per minute to 1.31 liters per minute. This very small change of air input is necessary to obtain adjustability at high $O_2$ percentages.

As can be seen from Table 1, even at maximum air opening (dial at 60%), and $O_2$ flow of 40 liters per minute, total output flow rate of the discharged mixture is below 80 liters per minute. Thus the very small size of the total air entrainment port area helps to prevent excessive output flow rates.

Importantly, the air entrainment port of the nebulizer described herein is easily adjustable in small relatively precise and repeatable amounts at relatively low entrained air flow rates. Stated differently, relatively large (and therefore easily controlled) movement of the dial results in relatively small changes in the air entrainment opening. Further, as the dial gets closer to the higher $O_2$ percentage positions, the rate of change of the air opening decreases to yield an increasing precision of air flow adjustment. This permits precise control of high $O_2$ percent content of the output mixtures while maintaining optimum total output flow rates.

Moreover, the small size air entrainment opening is itself divided into a plurality of smaller openings so as to prevent or substantially eliminate projection of droplets from the mixing chamber.

There has been disclosed an improved nebulizer capable of providing output mixture of very high oxygen content while limiting total output flow rates to reasonable and acceptable magnitudes without employing auxiliary pressurized air inputs.

The foregoing detailed description is to be clearly understood as given by way of illustration and example only, the spirit and scope of this invention being limited solely by the appended claims.

What is claimed is:

1. An air entrainment nebulizer comprising:

a mixer body having a mixing chamber and a pressurized gas input fitting, said mixer body having a discharge port for providing a total flow output of moisturized air having a selected oxygen content, a unitary one piece oxygen jet mounted in said body and connected to said fitting, said jet having an orifice for projecting a high velocity stream of oxygen into said mixing chamber at a rate of more than fifteen liters per minute, a liquid aspirating fitting mounted in said body adjacent said jet, an air entrainment opening formed in said mixer body in communication with said chamber and with ambient air, said entrainment opening having a maximum open area not greater than an area that flows air into the chamber at a rate that causes total flow output of a moisturized mixture of oxygen and air from said discharge port at a rate not greater than about eighty liters per minute when pressurized oxygen flows through said jet at a rate of not greater than forty liters per minute, and closure means mounted to said body and movable in a first direction between open and closed positions for progressively blocking and unblocking said opening to decrease the open area of said entrainment opening, said closure means and entrainment opening being configured and arranged to effect a rate of change of open area of said entrainment opening that decreases as said closure means moves toward said closed position, whereby the rate of air flow into said entrainment opening is adjustable in very small amounts when said closure means approaches said closed position, said air entrainment opening comprising a plurality of mutually adjacent narrow, elongated slots extending in mutually parallel side by side relation in said first direction, said slots having intermediate portions that are in overlapping relation and coextensive with each other along said first direction, and each said slot having an end that terminates at a different position along said first direction, whereby said slots are partly overlapped and longitudinally staggered in said first direction, said closure means having an edge that simultaneously cooperates with all of said slot intermediate portions to simultaneously change the length of blocked parts of all slots in intermediate positions between said closed and open positions, and cooperating with less than all of said slot ends to simultaneously change the length of less than all of said slots when in positions near said closed position, whereby the staggered relation of said slot ends effect a decreasing rate of closure when the closure means is near to and moving toward said closed position.

2. The nebulizer of claim 1 wherein said air entrainment opening comprises a plurality of slots each having a width not more than about 0.025 inches.

3. The nebulizer of claim 1 wherein said air entrainment opening comprises a port opening in said mixer body, a ridge on said body encircling said port opening and projecting from said body, and said closure means comprising a port closure member mounted in said mixer body for slidable motion over and in contact with said ridge between a first position in which said closure member contacts a major portion of said ridge to close said port opening, and a second position in which said closure member contacts a minimum portion of said ridge to open said port opening, said port closure member being spaced from said mixed body by said ridge.

4. The nebulizer of claim 3 wherein said closure member includes a slidable sleeve having a sleeve opening substantially aligned with said port opening when said closure member is in said second position.

5. The nebulizer of claim 4 wherein said slidable sleeve includes a shield portion adjacent said sleeve opening, said closure member being movable to at least one intermediate position in which said shield portion overlaps part of said port opening but is spaced therefrom by said ridge, to define a restricted air passage between said shield and said port opening, whereby in said intermediate position said shield portion will block projection of liquid from at least part of said port opening.

6. The nebulizer of claim 5 wherein said sleeve opening includes a primary section and a fine adjustment section extending from one side of said primary section, said fine adjustment section having an area that decreases with increase of distance from said primary section.

7. The nebulizer of claim 1 wherein the maximum open area of said entrainment opening is not more than 0.025 square inches, thereby limiting total flow output from said discharge port to a rate not greater than about eighty liters per minute when oxygen flows through said jet at forty liters per minute and said closure means is in said open position to completely unblock said air entrainment opening.

8. The nebulizer of claim 1 wherein each said slot has a maximum width of 0.025 inches, thereby preventing projection of water droplets from the mixing chamber.

9. The nebulizer of claim 1 wherein said closure means is mounted for motion to a first nearly closed position in which all but two of said slots are completely blocked and two are partly blocked and partly open, and to a second more nearly closed position in which all but one of said slots are completely blocked and one is partly blocked and partly open.

10. The nebulizer of claim 1 wherein said slots are tapered, being wider at the outside and have rounded edges between adjacent slots.

11. The nebulizer of claim 1 where each said slot has a length many times greater than its width.

* * * * *